United States Patent [19]

Krogsgaard-Larsen et al.

[11] Patent Number: 4,923,880

[45] Date of Patent: May 8, 1990

[54] 4,5,6,7-TETRAHYDROISOTHIAZOLO (4,5-C) PYRIDINE DERIVATIVES

[75] Inventors: Povl Krogsgaard-Larsen, Alleroed; Erik Falch, Vedbaek; Henrik Pedersen, Broenshoej, all of Denmark

[73] Assignee: H. Lundbeck A/S, Copenhagen-Valby, Denmark

[21] Appl. No.: 322,632

[22] Filed: Mar. 13, 1989

[30] Foreign Application Priority Data

Mar. 14, 1988 [GB] United Kingdom ............... 8806013
Sep. 26, 1988 [GB] United Kingdom ............... 8822564

[51] Int. Cl.$^5$ ..................... A61K 31/44; C07D 513/04
[52] U.S. Cl. .................................... 514/301; 546/114
[58] Field of Search ......................... 546/114; 514/301

[56] References Cited

PUBLICATIONS

Krogsgaard Larsen et al., J. Med. Chem., vol. 26, pp. 895–900, (1983).
Sauerberg et al., J. Med. Chem., vol. 29, pp. 1004–1009, (1986).

Primary Examiner—Mary C. Lee
Assistant Examiner—Bernard I. Dentz
Attorney, Agent, or Firm—Gordon W. Hueschen

[57] ABSTRACT

The present invention relates to novel compounds of the following formula:

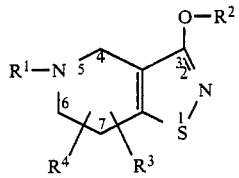

individual isomers and pharmaceutically acceptable acid addition salts thereof, wherein $R^1$ is hydrogen, alkyl or phenyl-lower alkyl, in which the phenyl group may be substituted with halogen, lower alkyl or lower alkoxy;

$R^2$ is alkyl, alkenyl, alkynyl, branched or unbranched, with 1–6 carbon atoms inclusive, which group may be optionally substituted with fluoro, hydroxy or phenyl optionally substituted with halogen, trifluoromethyl, lower alkyl, hydroxy or lower alkoxy;

$R^3$ and $R^4$ are the same or different, and each represents hydrogen, alkyl(1–6 C-atoms), cycloalkyl (3–6 C-atoms), phenyl optionally substituted with halogen trifluoromethyl, lower alkyl, hydroxy or lower alkoxy, or phenyl-lower alkyl, in which the phenyl group may be substituted with halogen, trifluoromethyl, lower alkyl, hydroxy or lower alkoxy.

The invention moreover relates to methods for the preparation of the compounds of formula I, to novel intermediates, to pharmaceutical compositions containing same and to methods for the treatment of disorders, caused by malfunction of the acetylcholine (AcCh) or muscarinic system, by administering a non-toxic effective amount of a compound of formula I.

9 Claims, No Drawings

4,5,6,7-TETRAHYDROISOTHIAZOLO (4,5-C) PYRIDINE DERIVATIVES

BACKGROUND OF THE INVENTION

AcCh is known to be a neurotransmitter in the peripheral as well as the central nervous system (CNS). Reduced function of AcCh in the CNS, probably as a result of degeneration of neurones utilizing AcCh as a neurotransmitter, is believed to be related to the etiology of various diseases such as Alzheimers disease and Down's syndrome (R. M. Marchbanks, *J. Neurochem.* 39 (1982) 9–15; R. D. Terry and P. Davies, *Ann. Rev. Neurosci.*, 3 (1980) 77; N. R. Sims, D. M. Bowen, S. J. Allen, C. C. T. Smith, D. Neary, D. J. Thomas and A. N. Davidson, *J. Neurochem.*, 40 (1983) 503–509; E. Roberts, in *Ann. New York Acad. Sci.* (F. Marott Sinex and C. R. Merril, editors), 396 (1982) 165–178. Furthermore, senile dementia, which may be associated with aging, appears to be somehow related to decreased AcCh activity in the CNS, and similarly impaired learning and memory functions have been associated with decreased functions of the central AcCh-system (P. S. Anderson and D. Haubrich, *Ann. Rep. Med. Chem.*, 16 (1981) 51–60.

Administrations of drugs which either increase the level of AcCh by blocking the enzymatic breakdown of the transmitter or directly stimulating the AcCh-receptor, AcCh-agonists, have been found to improve the cognitive malfunctions observed in patients with senile dementia of the Alzheimer type to various degrees (Christie et al., *Br.J.Psych.* 138 (1981) 138–146; Harbaugh et al., *Neuro-surgery* 15 (1984) 514–518; Beller et al., *Psychopharmacol.* 87 (1985) 147–151; Schwartz and Kohlstaedt, *Life Sci.* 38 (1986); Summers et al., *N.Engl.J.Med.* 315 (1986) 1241–1245. Compounds capable of activating the AcCh receptors are therefore of primary interest. However, most known AcCh agonists, including AcCh itself, contain quaternary ammonium groups and, consequently, these compounds do not penetrate the blood-brain barrier (BBB) easily after peripheral administration. As a result of this, such compounds do not reach the AcCh receptors in the CNS but activate almost exclusively the peripheral AcCh receptors, which are unrelated to the diseases mentioned above, provoking various undesired effects. Arecoline (methyl 1-methyl-1,2,5,6-tetrahydropyridine-3-carboxylate) is an AcCh agonist, which does not contain a quaternary ammonium group. Arecoline is a tertiary amine, and arecoline is capable of penetrating the BBB after peripheral administration. The ester group of arecoline is, however, very rapidly hydrolyzed in vivo, and arecoline has very weak and frequently negligible central effects after peripheral administration.

DESCRIPTION OF THE INVENTION

According to the present invention, it has now surprisingly been found that the novel compounds of Formula I have AcCh agonist activity which is about ten times that of the corresponding 3-alkoxyisoxazole-derivatives, which are known from U.S. Pat. No. 4,608,378.

In the design of these compounds great importance has been attached to the following facts:
1. The 3-alkoxyisothiazole units are isosteric with ester groups containing the same alkoxy groups. In contrast to ester groups the respective 3-alkoxyisothiazole units are not susceptible to hydrolysis under physiological conditions.
2. The $pK_a$ values are comparable with physiological pH values (pH 7.1–7.4). This means that considerable fractions of peripherally administered doses of the compounds will exist in the unionized form in the blood stream and, consequently, the compounds in all probability penetrate the BBB very rapidly.

The new compounds have high affinity to central cholinergic receptors, as measured by the ability of the compounds to displace tritiated oxotremorine-M from rat brain homogenates. The compounds have also high affinity to central muscarinic M-1 receptors, as defined by their ability to displace tritiated pirenzepine from rat brain homogenates. The potent central activity of the compounds in vivo can be demonstrated by the ability of the compounds to induce hypothermia in mice or to prevent isoniazid induced convulsions in mice. Compared with the potent central activity they show only minor peripheral side effects.

Moreover, the compounds of Formula I have very low toxicity as compared to therapeutic effective doses.

This invention also includes pharmaceutically acceptable salts of the compounds of Formula I formed with non-toxic organic or inorganic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, embonic, succinic, oxalic, bis methylenesalicylic, methanesulfonic, ethanedisulfonic, acetic, propionic, tartaric, salicylic, citric, glucomic, lactic, malic, mandelic, cinnamic, citraconic, aspartic, stearic, palmitic, itaconic, glycolic, p-aminobenzoic, glutamic, benzene sulfonic and theophylline acetic acids as well as the 8-halotheophyllines, for example 8-bromo-theophylline. Exemplary of such inorganic salts are those with hydrochloric, hydrobromic, sulfuric, sulfamic, phosphoric and nitric acids. Of course, these salts may also be prepared by the classical method of double decomposition of appropriate salts, which is well-known to the art.

In the present context, the term "alkyl" designates $C_{1-6}$ alkyl which may be straight or branched, such as methyl, ethyl, propyl, isopropyl, butyl, tert. butyl, pentyl or hexyl. Among the alkyl groups, lower alkyl groups are preferred. The term "lower alkyl" designates $C_{1-4}$ alkyl which may be straight or branched, such as methyl, ethyl, propyl, isopropyl, butyl, or tert.butyl. The term "alkenyl" designates a $C_3$–$C_6$ straight or branched alkyl group which contains a double bond, such as 2-propenyl, 2-butenyl, 2-pentenyl, 2-hexenyl, 2-methyl-2-propenyl or 3-methyl-2-butenyl. The term "alkynyl" designates a $C_3$–$C_6$ straight or branched alkyl group containing a triple bond, such as 2-propynyl, 2-butynyl, 2-pentynyl, 2-hexynyl or 4-methyl-2-pentynyl. The term "phenyl-lower-alkyl" designates a lower alkyl group (as herin defined) which, in turn, is substituted with a phenyl group. Preferred phenyl-lower-alkyl are benzyl, 1- and 2-phenylethyl, 1-, 2- and 3-phenylpropyl, and 1-methyl-1-phenylethyl. Where the phenyl group is substituted with halogen, lower alkyl, or lower alkoxy, they may be mono-, di- or tri-substituted, and when they are di- or tri-substituted the substituents may be the same or different. The term "lower alkoxy" designates such groups having from 1-6 carbon atoms inclusive. Preferred groups are methoxy and ethoxy. The term "halogen" designates F, Cl, Br, or I; Cl and Br are preferred.

Specific examples of preferred compounds of the Formula I are:

3-Methoxy-4,5,6,7-tetrahydroisothiazolo[4,5-c]pyridine
3-Ethoxy-4,5,6,7-tetrahydroisothiazolo[4,5-c]pyridine
3-(2-Propynyloxy)-4,5,6,7-tetrahydroisothiazolo[4,5-c]pyridine
3-Methoxy-7-methyl-4,5,6,7-tetrahydroisothiazolo[4,5-c]pyridine
7-Methyl-3-(2-propynyloxy)-4,5,6,7-tetrahydroisothiazolo[4,5-c]pyridine
5,7-Dimethyl-3-(2-propynyloxy)-4,5,6,7-tetrahydroisothiazolo[4,5-c]pyridine
7-Methyl-3-(2-propenyloxy)-4,5,6,7-tetrahydroisothiazolo[4,5-c]pyridine
5,7-Dimethyl-3-(2-propenyloxy)-4,5,6,7-tetrahydroisothiazolo[4,5-c]pyridine and salts thereof.

When $R^3$ and $R^4$ are different or the same at different positions, the compounds of Formula I can be separated in geometrical and/or optical isomers. Likewise, when $R^1$ contains a double bond the compounds of Formula I may exist in an E-and a Z-form. It is understood that the present invention encompasses all enantiomers and mixtures thereof, as well as both the E- and the Z-form and mixtures thereof.

Especially preferred compounds are:
7-Methyl-3-(2-propynyloxy)-4,5,6,7-tetrahydroisothiazolo[4,5-c]pyridine
(+)-7-Methyl-3-(2-propynyloxy)-4,5,6,7-tetrahydroisothiazolo[4,5-c]pyridine
(−)-7-Methyl-3-(2-propynyloxy)-4,5,6,7-tetrahydroisothiazolo[4,5-c]pyridine
5,7-Dimethyl-3-(2-propynyloxy)-4,5,6,7-tetrahydroisothiazolo[4,5-c]pyridine
(+)-5,7-Dimethyl-3-(2-propynyloxy)-4,5,6,7-tetrahydroisothiazolo[4,5-c]pyridine
(−)-5,7-Dimethyl-3-(2-propynyloxy)-4,5,6,7-tetrahydroisothiazolo[4,5-c]pyridine
7-Methyl-3-(2-propenyloxy)-4,5,6,7-tetrahydroisothiazolo[4,5-c]pyridine and salts thereof.

The compounds of Formula I may - according to the invention - be prepared by (a) reacting a compound of the Formula II

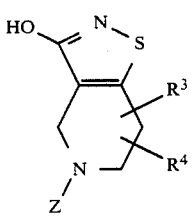
II in which $R^3$ and $R^4$ is as defined above and Z is an amino-protecting group readily removable, e.g. by hydrolysis or hydrogenation with a compound of the Formula III $R^2-X$     (III)

in which $R^2$ is as defined above, and X is a leaving group, and removing the group Z by hydrolysis or hydrogenation, or (b) reacting a compound of the Formula I, in which $R^1$ is hydrogen and $R^2$, $R^3$ and $R^4$ are as defined above, with an aldehyde of the Formula IV

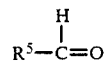
IV in which $R^5$ is hydrogen or lower alkyl, in the presence of a reducing agent, or (c) reacting a compound of the Formula I, in which $R^1$ is hydrogen and $R^2$, $R^3$ and $R^4$ are as defined above, with a compound of the general formula V

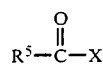
V in which $R^5$ and X are as defined above, and reducing the resulting compound of the following formula (VI):

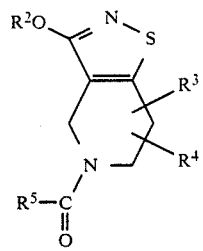
VI with a reducing agent (e.g. lithium aluminhydride, diborane, cyanoborohydride or the like), or (d) reacting a compound of the formula (VII)

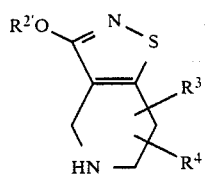
VII in which $R^{2'}$ is hydrogen or a group $R^2$ as defined above, and $R^3$ and $R^4$ are as defined, with a compound of formula (III), in which $R^2$ and X are as defined, or (e) reacting a compound of the Formula (VIII)

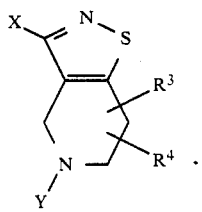
VIII in which Y is $R^1$ or Z as defined above, with an alcohol of the Formula (IX):

$R^2-OH$     (IX)

in which R² is as defined above, whereupon the compound of Formula I formed is isolated as the free base or a non-toxic pharmaceutically acceptable acid addition salt thereof and, if desired, the individual isomers are isolated.

Specific examples of Z in formulas (II) and (IV) are the following:

Methoxycarbonyl, ethoxycarbonyl, propoxycarbonyl, tert.butoxycarbonyl, benzyloxycarbonyl, 4-chlorobenzyloxycarbonyl, trityl, formyl or acetyl.

As examples of leaving groups X may be mentioned chlorine, bromine, iodide, and sulphate.

In method (a) the reaction is preferably performed in (1) a mixture of water and a waterimmiscible organic solvent, e.g. dichloromethane or toluene in the presence of a phase transfer catalyst, e.g. tetrabutylammonium hydrogen sulphate and a base, e.g. potassium carbonate, sodium hydroxide, or a tertiary amine, or (2) a solvent, e.g. acetone, a lower alcohol, toluene or N,N-dimethylformamide in the presence of a base, e.g. potassium carbonate, sodium hydroxide, a tertiary amine, or a metal alcoholate and, if convenient, a phase transfer catalyst, e.g. tetrabutylammonium hydrogen sulphate.

The reaction is carried out at a temperature from 0° C. to the boiling point of the solvent, and for a period of time from 1–96 hours. The removal of the group Z may be performed in wellknown manner, e.g. by hydrolysis or hydrogenation, and then, if desired, a group $R_1$ may be introduced by one of the methods (c) or (d).

In method (b) the reaction is performed in the presence of a reducing agent, e.g. formic acid, diborane or cyanoborohydride in a solvent, e.g. an ether, methanol, chloroform or dioxane, at a temperature from −20° C. to 100° C.

In method (c) the intermediate of formula VI is mostly not isolated but may be so, if desired. Otherwise, the compound of formula VI formed in the reaction mixture may without isolation be treated with a reducing agent, e.g. lithium aluminiumhydride, diborane or cyanoborohydride. The reaction may be performed in an inert solvent, e.g. an ether, toluene or dioxane, at a temperature from −20° C. to the boiling point of the solvent.

In method (d) the reaction is preferably performed in a solvent, e.g. acetone, a lower alcohol, toluene or N,N-dimethylformamide, in the presence of a base, e.g. potassium carbonate, a metal hydroxide, a tertiary amine or a metal alcoholate. The reaction is carried out at a temperature from 0° C. to the boiling point of the solvent, and for a period of time from 0 to 96 hours.

In method (e) the reaction is normally performed in a solution of excess of the alcohol of Formula IX, which may contain from 0% to 50% water, and in the presence of a base, e.g. a metal hydroxide or a metal alcoholate. The reaction temperature will usually be in the range of 0°–150° C., preferably from 0° C. to the boiling point of the alcohol of the Formula IX. In many cases, where Y is Z, especially when the reaction mixture contains water, the amino-protecting group Z is removed by hydrolysis during the reaction. Otherwise, the group Z may be removed in wellknown manner, e.g. by hydrolysis or hydrogenation, and then, if desired, a group $R^1$ may be introduced by one of the methods (c) or (d).

The preparation of the intermediates and compounds of Formula I will be illustrated in the following by examples which may not be construed as limiting.

The following litterature references are used:

(1) P. Krogsgaard-Larsen, H. Mikkelsen, P. Jacobsen, E. Faich, D. R. Curtis, M. J. Peet, and J. D. Leah, *J.Med.Chem.*, 26 (1983) 895–900.

(2) Eastman Kodak Co., U.S. Pat. No. 2,659,739 (1950).

EXAMPLE 1

Methyl 3-methoxy-4,5,6,7-tetrahydroisothiazolo[4,5-c]pyridine-5-carboxylate (2)

To a solution of 1.60 g (7.5 mmol) of methyl 3-hydroxy-4,5,6,7-tetrahydroisothiazolo[4,5-c]pyridine-5-carboxylate (1)[1] in ether (50 ml) and ethanol (2 ml) was added an excess of diazomethane. The mixture was stirred at room temperature for 1 hour, and the excess of diazomethane was destroyed by addition of glacial acetic acid. The mixture was evaporated in vacuo and the residue submitted to column chromatography on silica gel (eluent: toluene-ethyl acetate) yielding 890 mg of the title compound as a colourless oil.

¹H NMR (CDCl₃: 4.25 (2 H, s), 3.95 (3 H, s), 3.65 (3 H, s), 3.60 (2 H, t), 2.75 (2 H, t).

EXAMPLE 2

3-Methoxy-4,5,6,7-tetrahydroisothiazole[4,5-c]pyridine Hydrochloride (3)

To a solution of potassium hydroxide (2.02 g, 36 mmol) in methanol (9 ml) was added 0.89 g (3.9 mmol) of 2, and the mixture was refluxed for 20 hours. The reaction mixture was evaporated in vacuo. The residue was dissolved in water (30 ml) and extracted with three 50 ml portions of chloroform. The combined extracts were dried and evaporated. The residue was dissolved in ether, and an excess of a solution of hydrochloric acid in ethyl acetate was added. The precipitate was collected and recrystallized from methanol-ether yielding 0.70 g (87%) of the title compound. M.P. 234°–235° C. Anal. ($C_7H_{11}Cl\ N_2OS$),C,H,N.

EXAMPLE 3

Methyl 3-ethoxy-4,5,6,7-tetrahydroisothiazolo[4,5-c]pyridine-5-carboxylate (4)

A mixture of 1[1] (1.5 g, 7.0 mmol), tetrabutylammonium hydrogen sulphate (TBA, 2.5 g), sodium hydroxide (0.6 g), water (6 ml) and dichloromethane (6 ml) was stirred for 10 minutes. Diethylsulphate (1 ml) was added, and the mixture was heated to reflux overnight. Concentrated ammonium hydroxide (10 ml) was added, and the mixture was refluxed for 1 hour. The reaction mixture was diluted with dichloromethane, and the organic phase was washed 3 times with water, dried over magnesium sulphate, and evaporated in vacuo to yield a syrup (2.5 g), which was chromatographied on silica gel eluted with ethyl acetate -heptane (1:2). The first UV-active fraction yielded 4 (1.1 g), 65%) as a syrup.

¹H-NMR 1.35 ppm (triplet, 3H), 2.8 ppm (triplet, 2H), 3.74 ppm (singlet 3H, triplet 2H), 4.36 ppm (singlet, 2H), 4.37 ppm (quartet, 2H).

EXAMPLE 4

3-Ethoxy-4,5,6,7-tetrahydroisothiazolo[4,5-c]pyridine, maleate (5)

A solution of 4 (1.1 g, 4.5 mmol), potassium hydroxide (2.5 g) in water (2.5 ml) and methanol (25 ml) was refluxed overnight. The solution was evaporated to near dryness, and the residue was dissolved in dichloromethane. The solution was washed 3 times with saturated sodium chloride solution, dried over magnesium sulphate and evaporated in vacuo yielding syrupy 5 (0.4 g, 50%), which was crystallized from ethyl acetate as the maleate (0.6 g, 44%). M.P. 163°–165° C. Anal. ($C_{12}H_{16}N_2O_5S$), C,H,N.

EXAMPLE 5 tert.Butyl 3-hydroxy-4,5,6,7-tetrahydroisothiazolo[4,5-c]pyridine-5-carboxylate (7)

To a solution of 3-hydroxy-4,5,6,7-tetrahydroisothiazole [4,5-c]pyridinium bromide (6)[1] (2,4 g, 10 mmol) and potassium carbonate (2 g) in water (20 ml) was added a solution of pyrocarbonic acid di-tert.-butylester (2,5 g) in tetrahydrofurane (20 ml). The mixture was stirred for 2 hours, and then most of the tetrahydrofurane was evaporated in vacuo. The residue was diluted with water and was washed 3 times with ethyl acetate. Ethyl acetate (50 ml) was added to the aqueous phase, and the mixture was cooled in an ice bath and carefully acidified with hydrochloric acid to pH=3. The phases were separated, and the aqueous phase was further extracted 2 times with ethyl acetate. The combined organic phases were dried over magenesium sulphate and evaporated in vacuo to yield 7 (1.5 g, 58%). M.P. 174°–177° C.

EXAMPLE 6

3-(2-Propynyloxy)-4,5,6,7-tetrahydroisothiazole[4,5-c]pyridine, hemifumarate (8)

A mixture of 7 (1.5 g, 5.6 mmol), tetrabutylammonium hydrogen sulphate (0.3 g), potassium carbonate (2 g) and propargyl bromide (1.5 ml) in N,N-dimethylformamide (30 ml) was heated to 70° C. for 4 hours. The mixture was then left at room temperature overnight, then filtered, and the filtrate was evaporated in vacuo. The residue was dissolved in ether (50 ml), the the solution was washed 2 times with water, dried over magnesium sulphate and evaporated in vacuo. The resulting syrup was dissolved in ether, saturated with hydrogen chloride and stirred at room temperature for 2 hours. The reaction mixture was evaporated in vacuo, and the base of 8 was worked up with sodium hydroxyde in the usual manner, and the hemifumarate was crystallized from acetone (0.6 g, 55%). M.P. 186°–188° C. Anal. ($C_{11}H_{12}N_2O_3S$), C,H,N.

EXAMPLE 7

N-(2-Cyanoethyl)-2-methyl-3-aminopropionitrile (10)

A solution of 2-methyl-3-aminopropionitrile (9)[2] (197 g, 2.35 mol) and acrylonitrile (170 ml) in ethanol (250 ml) was refluxed overnight and then evaporated in vacuo to yield 10 (316 g, 98%) as a light oil.

EXAMPLE 8

Methyl 3-cyano-4-oxo-5-methylpiperidine-1-carboxylate (11)

To a well stirred solution of potassium tert.-butylate (270 g) in toluen (1.5 l) was slowly added 10 (316 g, 2.3 mol), and the mixture was stirred at reflux temperature for 1.5 hours. The mixture was cooled to room temperature and filtered. The wet filtercake was dissolved in 6N hydrochloric acid (2.5 l) and refluxed for 20 minutes. The mixture was cooled on an ice bath and neutralized with sodium hydroxide (pH=7, T<30° C.). More sodium hydroxide was added with cooling (185 g), and then methyl chloroformate (170 ml) was added at 10° C. After the addition the mixture was stirred for 1 hour at room temperature. The mixture was washed 2 times with ethyl acetate. The aqueous phase was acidified to pH=3 with concentrated hydrochloric acid and extracted 3 times with ethyl acetate. The combined extracts were washed twice with saturated sodium chloride solution, dried over magnesium sulphate and evaporated in vacuo to yield 11 (295 g, 63%) as as oil. Crystallization from ether gave 11 with M.P. 65°–68° C.

EXAMPLE 9

Methyl 3-cyano-4-oxo-5-methylpiperidine-1-carboxylate ethylene ketal (12)

A mixture of crude 11 (200 g, 1.02 mol), 4-toluenesulfonic acid (35 g), 1,2-ethanediol (900 ml), and 1,1,1-trichlorethane (1 liter) was refluxed with a water separator overnight. The mixture was cooled, water (1 liter) was added and the phases separated. The aqueous phase was extracted 3 times with dichloromethane, and the combined organic phases were washed once with dilute sodium hydroxide solution and once with saturated sodium chloride solution. Drying over magnesium sulphate and evaporation in vacuo of the organic phase yielded 12 (195 g, 80%) as an oil.

EXAMPLE 10

Methyl 3-carboxamido-4-oxo-5-methylpiperidine-1-carboxylate ethylene ketal (13)

To a solution of 12 (195 g, 0.81 mol) in ethanol (1 liter) was added a solution of sodium hydroxide in water (40 ml). Hydrogen peroxide (250 ml) was added keeping the temperature below 70° C. The mixture was stirred at 60° C. for 3 hours, and 28% sodium hydroxide (15 ml) and hydrogen peroxide (250 ml) were added. The mixture was stirred at 55° C. overnight and evaporated in vacuo. The semicrystalline residue was dissolved in dichloromethane, the the solution was washed twice with saturated sodium chloride solution. Drying over magnesium sulphate and evaporation in vacuo yielded 13 (139 g, 67%) as sticky broad melting crystals.

EXAMPLE 11

Methyl 3-carboxamido-4-oxo-5-methylpiperidine-1-carboxylate (14)

A solution of 13 (129 g, 0.50 mol) in 6N hydrochloride acid (0.5 l) was left for 4 hours at room temperature. The solution was neutralized with solid sodium hydroxide (pH=7) with cooling. The solution was evaporated in vacuo, and the semicrystalline residue was extracted with boiling acetone. The acetone solution was cooled, filtered, and evaporated in vacuo to yield 14 (80 g, 75%) as sticky broad melting crystals.

EXAMPLE 12

Methyl 3-carboxamido-4-benzylamino-5-methyl-1,2,5,6-tetrahydropyridine-1-carboxylate (15)

A solution of 14 (80 g, 0.37 mol) and benzylamine (50 ml) in p-xylene (500 ml) was heated to reflux with a water separator for 2 hours. On cooling to room temperature the product crystallized. The solid was filtered off, washed with p-xylene and dried to yield 15 (51 g, 45%), M.P. 195°–200° C.

EXAMPLE 13

Methyl 3-hydroxy-7-methyl-4,5,6,7-tetrahydroisothiazolo[4,5-c]pyridine-5-carboxylate (16)

Dry hydrogen sulfide was bobbled through dry N,N-dimethylformamide (0.5 l) for 1 hour with cooling on an ice bath. Then 15 (51 g, 0.17 mol) was added, and the mixture was stirred at 0° C. for 4 hours and then at room temperature overnight. The solution was evaporated in vacuo, and the residue was dissolved in ethyl acetate (175 ml). Bromine (45 ml) in ethyl acetate (100 ml) was added dropwise with cooling (T<10° C.). The solution was then stirred for 24 hours at room temperature. Cracked ice (100 g) was added and the mixture was made basic with 28% sodium hydroxide solution (T<20° C.). The aqueous phase was washed twice with ether and then acidified to pH=3 with concentrated hydrochloric acid. Extraction with dichloromethane, drying of the organic phase and evaporation in vacuo yielded crude 16 (11 g), which was eluted on silica gel with ethyl acetate - methanol -formic acid (95:5:1). This yielded pure 16 (7.7 g, 20%), $^1$H-NMR (DMSO-d$_6$) 2.18 ppm (dublet, J=4 Hz, 3 H), 3.13 ppm (broad multiplet, 1 H), 3.50 ppm (broad singlet, 2 H), 3.69 ppm (singlet, 3 H), 4.21 ppm (broad singlet, 2 H), 9.70 ppm (singlet, 1 H).

EXAMPLE 14 tert.Butyl-3-hydroxy-7-methyl-4,5,6,7-tetrahydroisothiazolo[4,5-c]pyridine-5-carboxylate (17)

A solution of 16 (3.7 g, 16.2 mol) in acetic acid saturated with hydrogen bromide (25 ml) was left overnight at room temperature and was then evaporated in vacuo.

From this crude product, 17 was prepared in analogy with the procedure described in Example 5.

Yield of oily 17 was 1.3 g (30%).

EXAMPLE 15

3-Methoxy-7-methyl-4,5,6,7-tetrahydroisothiazolo[4,5-c]pyridine, fumarate (18)

A mixture of 17 (1.7 g, 6.3 mmol), tetrabutylammonium hydrogen sulphate (2.5 g), sodium hydroxide (0.6 g), water (6 ml) and dichloromethane (6 ml) was stirred for 10 minutes. Dimethyl sulphate (1 ml) was added, and the mixture was refluxed overnight. Concentrated ammonium hydroxide (10 ml) was added, and the mixture was refluxed for 1 hour. The reaction mixture was diluted with dichloromethane, and the organic phase was washed 3 times with water, dried over magnesium sulphate and evaporated in vacuo to yield an oil (1.2 g), which was eluted from silica gel with ethyl acetate - heptane (1:2). The first UV-active fraction was dissolved in ether saturated with hydrogen chloride and stirred for 2 hours at room temperature. The reaction mixture was evaporated in vacuo, and the base of 18 was worked up in the usual manner, and the fumarate was crystallized from acetone. Yield of 18:0.35 g (18%), M.P. 167°–168° C. (dec.). Anal. (C$_{11}$H$_{16}$N$_2$O$_5$S), C,H,N.

EXAMPLE 16

7-Methyl-3-(2-propynyloxy)-4,5,6,7-tetrahydroisothiazolo[4,5-c]pyridine, fumarate (19)

Compound 19 was prepared from 17 (1,3 g, 4:8 mmol) in analogy with the procedure described in Example 6.

Yield of 19 was 0.32 g (20%). M.P. 184°–186° C. (dec.). Anal. (C$_{14}$H$_{16}$N$_2$O$_5$S), C,H,N.

EXAMPLE 17

(+)-7-Methyl-3-(2-propynyloxy)-4,5,6,7-tetrahydroisothiazolo[4,5-c]pyridine, fumarate (20) and (−)-7-Methyl-3-(2-propynyloxy)-4,5,6,7-tetrahydroisothiazolo[4,5-c]pyridine, fumarate (21)

To a solution of 19-base (7.5 g, 0.036 mol) in ethanol (20 ml) was added a solution of dibenzoyl-D-tartaric acid (3.22 g, 0.009 mol) in ethanol (20 ml). The crystals were filtered off and recrystallized twice from ethanol/water. Yield: 4.5 g, M.P. 169°–170° C. The dibenzoyl-D-tartrate was transformed into the fumarate in a conventional manner. Yield of 20:3.3 g (0.010 mol, 28%), M.P. 169°–170° C., $[\alpha]_D$=+39.8° (c. 0.5, water). Anal. (C$_{14}$H$_{16}$N$_2$O$_5$S), C,H,N.

To the mother liquor from the precipitation of the dibenzoyl-D-tartrate was added a solution of dibenzoyl-L-tartaric acid, monohydrate (3.22 g, 0.009 mol) in ethanol (20 ml). The product was treated as described above. Yield of 21:3.05 g (0.009 mol, 25%), M.P. 168°–169° C., $[\alpha]_D$=−40.4° (c=0.5, water). Anal. (C$_{14}$H$_{16}$N$_2$O$_5$S), C,H,N.

EXAMPLE 18

(−+)-5,7-Dimethyl-3-(2-propynyloxy)-4,5,6,7-tetrahydroisothiazolo[4,5-c]pyridine, oxalate (22)

A solution of 19-base (1,5 g, 7.2 mmol) in formic acid (25 ml) and 35% aqueous formaldehyde (10 ml) was heated to 70° C. for 4 hours. The reaction mixture was evaporated in vacuo and dissolved in water (50 ml). The solution was made basic (pH>12) with concentrated sodium hydroxide solution. The mixture was then extracted three times with dichloromethane, and the combined organic phases were washed twice with saturated brine. Drying over magnesium sulphate and evaporation in vacuo yielded an oil (0.9 g) from which the title oxalate was crystallized from acetone. Yield: 1.05 g (3.4 mmol), 47%), M.P.: 135°–140° C. Anal. (C$_{13}$H$_{16}$N$_2$O$_5$S), C,H,N.

EXAMPLE 19

(+)-5,7-Dimethyl-3-(2-propynyloxy)-4,5,6,7-tetrahydroisothiazolo[4,5-c]pyridine, oxalate (23) and (−)-5,7-Dimethyl-3-(2-propynyloxy)-4,5,6,7-tetrahydroisothiazolo[4,5-c]pyridine, oxalate (24)

The title compounds were synthesized as described in Example 18 from 20-base (1.5 g, 7.2 mmol) and 21-base (1.5 g, 7.2 mmol) respectively.

Yield of 23 (from 20) 1.1 g (3.5 mmol, 49%), [α]$_D$=+42.5° (c. 0.5, water), M.P. 151°–153° C. Anal. (C$_{13}$H$_{16}$N$_2$O$_5$S), C,H,N.

Yield of 24 (from 21) 1.5 g (4.8 mmol, 67%), [α]$_D$=−41.6° (c. 0.5, water), M.P. 156°–157° C. Anal. (C$_{13}$H$_{16}$N$_2$O$_5$S), C,H,N.

EXAMPLE 20

(−+)-7-Methyl-3-(2-propenyloxy)-4,5,6,7-tetrahydroisothiazolo[4,5-c]pyridine, fumarate (25)

A mixture of 16 (2 g, 9.3 mmol), tetrabutylammonium hydrogen sulphate (0.45 g), potassium carbonate (3 g), allyl bromide (1.7 ml) and dimethylformamide (36 ml) was heated to 70° C. for 4 hours with stirring and was then stirred at room temperature for 12 hours. The mixture was filtered and evaporated in vacuo. The residue was dissolved in ethyl acetate, and the solution was washed twice with water and once with saturated brine. Drying over magnesium sulphate and evaporation in vacuo yielded an oil (2.37 g) which was eluted from silica gel with ethyl acetate - heptane (1:1). This yielded 1.3 g of an oil which was dissolved in a mixture of methanol (30 ml), water (3 ml), and potassium hydroxide (3 g). The mixture was refluxed for 48 hours and was then evaporated in vacuo. The residue was dissolved in dichloromethane and water, and the organic phase was extracted with dilute hydrochloric acid. The acidic aqueous phase was washed once with dichloromethane and was then made basic with concentrated sodium hydroxide solution. The aqueous phase was extracted three times with dichloromethane, and the combined organic phases were washed twice with saturated brine. Drying over magnesium sulphate and evaporation in vacuo yielded an oil (0.7 g) from which the title fumarate was crystallized from acetone. Yield: 0.85 g (2.6 mmol, 28%), M.P. 162°–164° C. Anal. (C$_{14}$H$_{18}$N$_2$O$_4$S), C,H,N.

The following tests were used to assess the pharmacological effects of the compounds of Formula I.

$^3$H-oxotremorine M binding was performed essentially as described by Birdsdall et al., 1980. Briefly, rat brains were homogenized in 100 vol (w/v) 10 mM Na,K-phosphate buffer (pH 7.4) and aliquots incubated with $^3$H-oxotremorine M (84.9 Ci/mmol, NEN) alone or in the presence of test compound in a total volume of 1.5 ml for 40 min. at 30° C. The reaction was stopped by adding 5 ml ice-cold buffer and filtered through Whatman GF/B filters soaked previously in 0.1% polyethylenimin (Sigma) for minimum 30 min. The filters were washed once with the same volume of buffer, transferred to scintillation vials and extracted in scintillation fluid (Pico-fluor 15, Packard) for at least two hours before counted in a liquid scintillation spectrometer (Beckman LS 1800). Non-specific binding was estimated at 10 μM atropine and all estimations made in triplicate. At least two displacement curves were made for each compound tested.

$^3$H-pirenzepine binding was performed essentially as described by Watson et al., 1983, the conditions being very much the same as for $^3$H-oxotremorine binding, except that aliquots were incubated with 1.0 nM $^3$H-pirenzepine for 60 min. at 25° C. and that the reaction was stopped by direct filtration followed by 3 washes with 4 ml buffer.

Birdsdall N. J. M., Hulme E. C., and Burgen A, S. V. (1980). "The Character of Muscarinic Receptors in Different Regions of the Rat Brain". Proc.Roy.Soc. London (Series B) 207,1.

Watson M., Yamamura H. I., and Roeske W. R. (1983). "A unique regulatory profile and regional distribution of $^3$H -pirenzepine binding in the rat provide evidence for distinct M$_1$ and M$_2$ muscarinic receptor subtypes". Life Sci. 32, 3001–3011.

| | RESULTS | |
|---|---|---|
| | $^3$H-Oxo-M IC$_{50}$ (nM) | $^3$H-Pirenzepine IC$_{50}$ (nM) |
| Compound 3 | 18 | 1700 |
| Compound 5 | 29 | 370 |
| Compound 8 | 6.3 | 53 |
| Compound 18 | 24 | 130 |
| Compound 19 | 1.8 | 6.9 |
| Compound 20 | 1.6 | 5.5 |
| Compound 21 | 0.93 | 8.1 |
| Compound 22 | 5.3 | 6.7 |
| Compound 23 | 18 | 14 |
| Compound 24 | 3.8 | 4.3 |
| Compound 25 | 5.3 | 11 |
| Arecoline | 1.9 | 1060 |
| (+)-O-propargyl-7-Me-THPO(*) | 18 | 61 |

(*)(+)-7-methyl-3-(2-propynyloxy)-4,5,6,7-tetrahydroisoxazolo [4,5-c]pyridine

This clearly demonstrates that the most prominent isothiazolo-compound of Formula I is far superior to the corresponding isoxazolo derivative.

The compounds of Formula I and the non-toxic acid addition salts thereof may be administered to animals such as dogs, cats, horses, sheeps or the like, including human beings, both orally and parenterally, and may be used for example in the form of tablets, capsules, powders, syrups or in the form of the usual sterile solutions for injection. Results upon administration to human beings have been very gratifying.

Most conveniently the compounds of Formula I are administered orally in unit dosage form such as tablets or capsules, each dosage unit containing the free amine or a non-toxic acid addition salt of one of the said compounds in a amount of from about 0.10 to about 100 mg, most preferably, however, from about 5 to 50 mg, calculated as the free amine, the total daily dosage usually ranging from about 1.0 to about 500 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

Typical examples of formulas for composition containing (+)-7-Methyl-3-(2-propynyloxy)-4,5,6,7-tetrahydroisothiazolo[4,5-c]pyridine, fumarate (called Compound 20 for short) as the active ingredient, are as follows:

| 1 Tablets containing 5 milligrams of Compound 20 calculated as the free base | |
|---|---|
| Compound 20 | 5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |

-continued

| 2 Tablets containing 50 milligrams of Compound 20 calculated as the free base | |
|---|---|
| Compound 20 | 50 mg |
| Lactose | 16 mg |
| Potato starch | 45 mg |
| Saccharose | 106 mg |
| Sorbitol | 6 mg |
| Talcum | 9 mg |
| Gelatine | 4 mg |
| Povidone | 3 mg |
| Magnesium stearate | 0.6 mg |
| 3 Syrup containing per milliliter | |
| Compound 20 | 10 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |
| 4 Solution for injection containing per milliliter | |
| Compound 20 | 50 mg |
| Acetic acid | 17.9 mg |
| Sterile water | ad 1 ml |
| 5 Solution for injection containing per milliliter | |
| Compound 20 | 10 mg |
| Sorbitol | 42.9 mg |
| Acetic acid | 0.63 mg |
| Sodium hydroxide | 22 mg |
| Sterile water | ad 1 ml |

Any other pharmaceutical tableting adjuvants may be used provided that they are compatible with the active ingredient, and additional compositions and dosage forms may be similar to those presently used for neuroleptics, analgesics or antidepressants.

Also combinations of the compounds of Formula I as well as their non-toxic acid salts with other active ingredients, especially other neuroleptics, thymoleptics, tranquilizers, analgetics or the like, fall within the scope of the present invention.

As previously stated, when isolating the compounds of Formula I in the form of an acid addition salt the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethane-sulphonates, lactates, citrates, tartrates or bitartrates, pamoates and maleates of the amines of Formula I. Other acids are likewise suitable and may be employed if desired. For example: fumaric, benzoic, ascorbic, succinic, salicylic, bismethylenesalicylic, propionic, gluconic, malic, malonic, mandelic, cannamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals, involving the neurotransmitters acetylcholine and muscarine, by administering to a living animal body, including human beings, an adequate quantity of a compound of Formula I or a non-toxic acid addition salt thereof. An adequate quantity would be from about 0.001 mg to about 10 mg per kg of body weight in each unit dosage, and from about 0.003 milligrams to about 7 milligrams/kg of body weight per day.

It is to be understood that the invention is not limited to the exact details of operation or exact compound or compositions shown and described, as obvious modifications and equivalents will be apparent to one skilled in the art.

What we claim is:

1. A compound of the following formula:

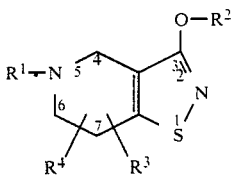

individual isomers and pharmaceutically acceptable acid addition salts thereof, wherein $R^1$ is hydrogen, alkyl or phenyl-lower alkyl, in which the phenyl group may be substituted with halogen, lower alkyl or lower alkoxy;

$R^2$ is alkyl, alkenyl, alkynyl, branched or unbranched, with 1-6 carbon atoms inclusive, which group may be optionally substituted with fluoro, hydroxy or phenyl optionally substituted with halogen, trifluoromethyl, lower alkyl, hydroxy or lower alkoxy;

$R^3$ and $R^4$ are the same or different, and each represents hydrogen, alkyl (1-6 C-atoms), cycloalkyl (3-6 C-atoms), phenyl optionally substituted with halogen trifluoromethyl, lower alkyl, hydroxy or lower alkoxy, or phenyl-lower alkyl, in which the phenyl group may be substituted with halogen, trifluoromethyl, lower alkyl, hydroxy or lower alkoxy.

2. A compound according to claim 1, wherein $R^1$ is hydrogen or alkyl, $R^2$ is alkyl, alkenyl or alkynyl, $R^3$ is hydrogen or alkyl, and $R^4$ is hydrogen.

3. A compound according to claim 1, which is selected from:

(−+)-7-Methyl-3-(2-propynyloxy)-4,5,6,7-tetrahydroisothiazolo[4,5-c]pyridine (+)-7-Methyl-3-(2-propynyloxy)-4,5,6,7-tetrahydroisothiazolo[4,5-c]pyridine (−)-7-Methyl-3-(2-propynyloxy)-4,5,6,7-tetrahydroisothiazolo[4,5-c]pyridine (−+)-5,7-Dimethyl-3-(2-propynyloxy)-4,5,6,7-tetrahydroisothiazolo[4,5-c]pyridine (−)-5,7-Dimethyl-3-(2-propynyloxy)-4,5,6,7-tetrahydroisothiazolo[4,5-c]pyridine as well as pharmaceutically acceptable acid addition salts thereof.

4. A compound of claim 1 being (+)-7-Methyl-3-(2-propynyloxy)-4,5,6,7-tetrahydroisothiazolo[4,5-c]pyridine and pharmaceutically acceptable acid addition salts thereof.

5. A pharmaceutical composition suitable for treating acetylcholine or muscarinic system disorders, in unit dosage form comprising, as an active ingredient, a compound as defined in claims 1, 2, 3 or 4, and one or more pharmaceutical diluents or carriers.

6. A pharmaceutical composition in unit dosage form, according to claim 5, wherein the active ingredient is present in an amount from 0.1 to 100 milligrams per unit dosage.

7. A pharmaceutical composition of claim 5 comprising, as active ingredient, the compound (+)-7-methyl-3-(2-propynyloxy)-4,5,6,7-tetrahydroisothiazolo [4,5-c] pyridine or a pharmaceutically-acceptable acid addition salt thereof.

8. Method of treating a subject suffereing from a malfunction of the acetylcholine or muscarinic system, comprising the step of administering to the said subject an effective amount of a compound of claim 1.

9. Method of claim 8, wherein the compound administered is (+)-7-methyl-3-(2-propynyloxy)-4,5,6,7-tetrahydroisothiazolo [4,5-c] pyridine or a pharmaceutically-acceptable acid addition salt thereof.

* * * * *

UNITED STATES PATENT AND TRADEMARK OFFICE
CERTIFICATE OF CORRECTION

PATENT NO. : 4,923,880

DATED : May 8, 1990

INVENTOR(S) : Povl Krogsgaard-Larsen, Erik Falch, Henrik Pedersen

It is certified that error appears in the above-identified patent and that said Letters Patent is hereby corrected as shown below:

```
Column 6, line 4; "litterature" should read -- literature --.
Column 7, line 36; "magenesium" should read -- magnesium --.
Column 7, line 51; delete "the", second occurrence.
Column 8, line 55; delete "the", first occurrence.
Column 12, line 31; "sheeps" should read -- sheep --.
Column 12, line 41; "a" should read -- an --.
```

Signed and Sealed this

Fourth Day of June, 1991

Attest:

HARRY F. MANBECK, JR.

Attesting Officer

Commissioner of Patents and Trademarks